(12) United States Patent
Sztejnberg et al.

(10) Patent No.: US 8,592,344 B2
(45) Date of Patent: Nov. 26, 2013

(54) PESTICIDAL COMPOSITIONS COMPRISING 4,5-DIHYDROXYINDAN-1-ONE

(75) Inventors: Abraham Sztejnberg, Rehovot (IL); Uri Gerson, Rehovot (IL); Zahi Paz, Gedera (IL); Zohar Kerem, Rehovot (IL); Izhak Bilkis, Gedera (IL)

(73) Assignee: Yissum Research Development Company of The Hebrew University of Jerusalem Ltd, Jerusalem (IL)

( * ) Notice: Subject to any disclaimer, the term of this patent is extended or adjusted under 35 U.S.C. 154(b) by 19 days.

(21) Appl. No.: 13/496,469

(22) PCT Filed: Sep. 13, 2010

(86) PCT No.: PCT/IL2010/000747
§ 371 (c)(1),
(2), (4) Date: Mar. 15, 2012

(87) PCT Pub. No.: WO2011/033502
PCT Pub. Date: Mar. 24, 2011

(65) Prior Publication Data
US 2012/0283097 A1 Nov. 8, 2012

Related U.S. Application Data

(60) Provisional application No. 61/242,829, filed on Sep. 16, 2009.

(51) Int. Cl.
*A01N 63/00* (2006.01)
*A01N 35/00* (2006.01)
*A61K 39/02* (2006.01)

(52) U.S. Cl.
USPC ............ 504/117; 504/145; 504/146; 504/348

(58) Field of Classification Search
None
See application file for complete search history.

(56) References Cited

PUBLICATIONS

AM Campbell et al., Xenognosin sensing in virulence: is there a phenol receptor in *Agrobacterium tumefaciens*?, Chemistry & Biology, vol. 7 No. 1, 2000, 65-76.*

* cited by examiner

*Primary Examiner* — Alton Pryor
(74) *Attorney, Agent, or Firm* — Dicke, Billig & Czaja

(57) ABSTRACT

Provided are pesticidal compositions comprising 4,5-dihydroxyindan-1-one or derivatives thereof for protecting important crops against mites, fungi, and bacteria. The compositions may be manufactured by fractionating fungal extracts.

4 Claims, 9 Drawing Sheets

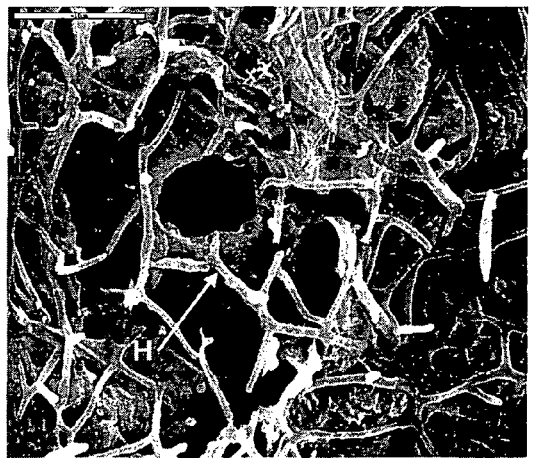
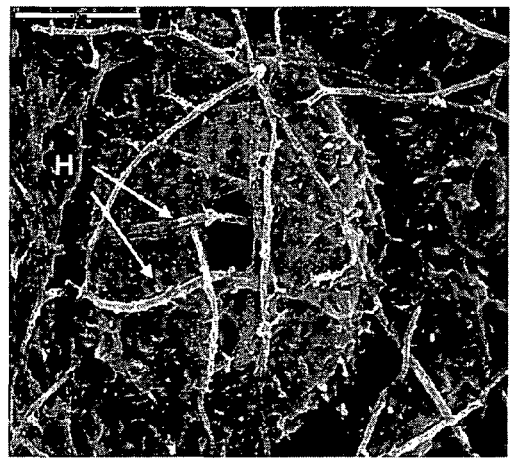
Fig. 12A                Fig. 12B
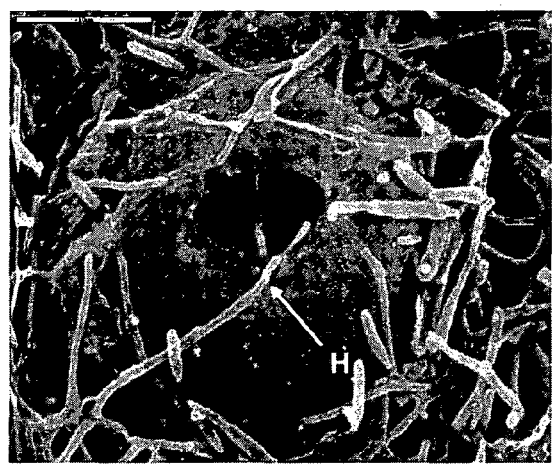
Fig. 12C

PESTICIDAL COMPOSITIONS COMPRISING 4,5-DIHYDROXYINDAN-1-ONE

FIELD OF THE INVENTION

The present invention relates to pesticidal compositions containing a fungal metabolite based on dihydroxyindane, particularly compositions for controlling mites, fungi, and bacteria causing damage to important crops.

BACKGROUND OF THE INVENTION

Plant diseases caused by mites, bacteria and fungi have a significant adverse impact on the production of important crops worldwide. The most important mites include spider mites, causing damages to many fruits, vegetables, and flowers. Examples include the two-spotted spider mite and the citrus rust mite. Chemical control has met with increasing difficulties, among others the development of resistance to pesticides, and to regulatory issues. Fungi secrete a wide range of secondary metabolites, of which many are toxic to other organisms and microorganisms, and may be used for biocontrol in agricultural systems. It is therefore an object of this invention to provide a method of controlling crop pests, employing fungal metabolites.

It is another object of this invention to provide a pesticide for protecting important crops against mites, bacteria and fungi.

It is still another object of this invention to provide an acaricide derived from fungi.

It is a further object of this invention to provide an acaricidal composition for protecting plants, including their fruits, susceptible to mites, bacteria and fungi.

It is a still further object of this invention to provide a method of controlling and preventing the infestation by mites and eventually other pests (including bacteria and fungi), comprising applying fungus-derived components.

It is also an object of this invention to provide a method of preparing a pesticidal formulation for protecting plants susceptible to mites, bacteria and fungi, such as citrus fruits.

Other objects and advantages of present invention will appear as description proceeds.

SUMMARY OF THE INVENTION

The present invention provides a pesticidal composition comprising as an active ingredient a compound of formula I

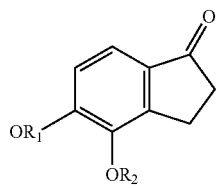

I wherein $R_1$ and $R_2$ are independently selected from H, $C_{1-18}$ alkyl, and $C_{1-18}$ acyl. As the present invention demonstrates the pesticidal activity of 4,5-dihydroxyindan-1-one, a skilled person will appreciate that derivatives which are easily metabolized in the pests' bodies to 4,5-dihydroxyindan-1-one will also be toxic for said pests. An example of such derivatives is 4,5-dihydroxyindan-1-one esterified on one or both hydroxyls by a carboxylic acid. In a preferred embodiment, said pesticidal composition comprises an extract from a fungus. A preferred fungus is *Meira argovae*. A pesticidal composition according to the invention preferably exhibits acaricides and fungicidal activity. Said pesticidal composition further preferably exhibits bactericide activity, such as against *Agrobacterium tumefaciens*.

The invention is directed to a composition for the use in controlling or preventing mite, fungi or bacterial infestation in a commercial plant, such as important crops, for example comprising fruit trees, vegetables, ornamental flowers, etc.

The mites may be, for example, spider mites. The composition may further comprise at least one component selected from the group consisting of agriculturally acceptable carrier, diluent, emulsifier, dispersant, and an additional active ingredient selected from herbicides, insecticides, growth stimulators, and fertilizers.

In another aspect of the invention, the present invention concerns an antibacterial composition comprising an extract from at least one of the fungus *Meira argovae*, *Meira geulakonigae*, or *Acaromyces ingoldii* progeny, mutants or variants thereof retaining the activity against bacteria, or biological products derived from said extracts.

The present invention further concerns a method for controlling bacterial infestation in plants comprising applying to the plant or to the vicinity of the plant an antibacterial composition comprising an extract from at least one of the fungi *Meira argovae*, *Meira geulakonigae*, or *Acaromyces ingoldii* progeny, mutants or variants thereof retaining the activity against bacteria, or biological products derived from said extracts.

Preferably the extract is from the fungus *Meira argovae*.

The fungus *Meira argovae*, is preferably the fungus designated CBS Accession No. 110053, progeny, mutants or variants thereof that retain the antibacterial activity.

The *Meira geulakonigae* is preferably designated CBS Accession No. 110052, progeny, mutants or variants thereof retaining the anticaterial activity.

The *Acaromyces ingoldii*, is preferably the fungus designated CBS Accession No. 110050, progeny, mutants or variants thereof retaining the antibacterial activity.

Preferably the composition comprises an extract from the fungus *Meira argovae*, and it exhibits in addition to antibacterial activity also acaricidal and fungicidal activities. In an important embodiment, the composition according to the invention comprises a compound of formula II

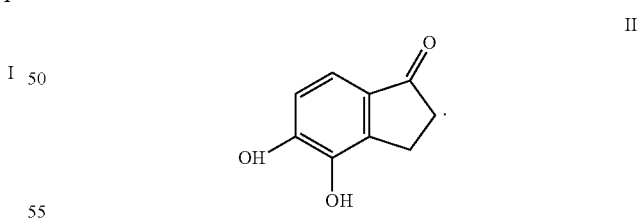

II

The invention provides a method of controlling mite, fungi or bacterial infestation in a plant susceptible thereto, comprising applying onto the plant or in the vicinity of said plant a composition comprising a compound of formula I, as described above, for example a compound of formula II. In the method according to the invention, said composition has preferably acaricidal, fungicidal and bactericidal activities; said plant usually comprises fruits, vegetables, or ornamental flowers. Examples of the mites to be controlled may include, without any limitations, the two-spotted spider mite and the citrus rust mite.

The invention relates to a method of manufacturing the composition comprising a compound of formula I

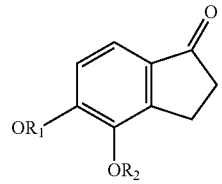

wherein $R_1$ and $R_2$ are independently selected from H, $C_{1-18}$ alkyl, and $C_{1-18}$ acyl, comprising cultivating a fungus, extracting the culture medium, and chromatographically separating the metabolites of said fungus released into said medium, and further optionally derivatizing said metabolite. In a preferred embodiment of the invention, the method of manufacturing the pesticidal composition comprises producing a metabolite of formula II

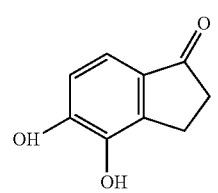

wherein the production is increased by adjusting the pH in the cultivating medium.

BRIEF DESCRIPTION OF THE DRAWINGS

The above and other characteristics and advantages of the invention will be more readily apparent through the following examples, and with reference to the appended drawings, wherein:

FIG. 1. shows separation of an active fungal agent.

FIG. 6. shows the dose response of the citrus rust mite to RPLC-purified toxin (argovin) of *Meira argovae*;

FIG. 7. is a graph showing the citrus rust mite mortality in response to applications of *Meira argovae* conidia ($10^8$ ml$^{-1}$) on ripe grapefruits (♦), untreated ripe grapefruits (control) (▲), and fungal-treated raw fruits (■), compared to raw untreated fruits (control) (●); the pH values of grapefruit peels were measured in both ripe and raw fruits;

FIG. 12. presents SEM micrographs of the hyphae of the FBAs penetrating into the skin of an orange (*Citrus sinensis* cv. New Hall); FIG. 12A shows *Acaromyces ingoldii*, FIG. 12B *Meira argovae*, and FIG. 12C *Meira geulakonigii*; large pits in the middle of the micrographs are stomata; arrows headed by an H point at the hyphae of the FBAs; the bars in the top left corner represent 10 μm.

DETAILED DESCRIPTION OF THE INVENTION

It has now been found that an HPLC fraction of the crude extract from the fungus *Meira argovae* exhibits a surprisingly strong acaricide activity. Furthermore, the same fraction shows also an antibacterial activity, when checked on an important crop pest, *Agrobacterium tumefaciens*. Such an unexpected advantageous combination of bioactivities forms an excellent base for manufacturing new pesticidal formulations.

Metabolites of the fungus *Meira argovae* were assayed as antagonists of mites and bacteria. Separation of extracted fungal metabolites by reversed phase liquid chromatography (RPLC), with subsequent testing of the obtained fractions, allowed to the present inventors to isolate a single mite-antagonistic fraction that comprises one major component. This active compound, named "argovin" herein, was identified by analysis of its spectral characteristics as 4,5-dihydroxyindan-1-one. This compound has been previously described only as a product or intermediate of chemical reactions; here, the compound has been isolated as a naturally occurring material, from a metabolite mixture. The growth rate of the fungus was higher at a neutral pH than at an acidic one. *Meira argovae* adjusts the pH of its media to values optimal for its colony growth and toxic secretions. RPLC-cleaned argovin, at 0.2 mg/ml, killed 100% of a population of the citrus rust mite, *Phyllocoptruta oleivora*. Conidia of *M. argovae*, when applied onto mite-infested ripe grapefruits, caused high mite mortality, as compared to mortality on infested unripe grapefruits. This may have been due to differences in the pH values of the peels: 6.7 for the ripe fruit and 5.6 for the unripe one. The inventors conclude that the fungus exploits the changing pH conditions on grapefruits for maximal toxin secretion, thereby causing higher mite mortality rates. This trait may be used and manipulated to control citrus rust mites in the field, as well as for toxin production for industrial and pharmaceutical uses. Agrovin is, thus, a novel natural product, antagonistic to mites, produced by the fungus *Meira argovae*, whose secretion is affected by ambient pH. Surprisingly and advantageously, the same material turned out to have also a bactericide activity, when checked on *Agrobacterium tumefaciens*—the bacterial causal agent of tumor formation in many agriculturally important plants, belonging among economically most important crop pathogens.

Figure 1A:
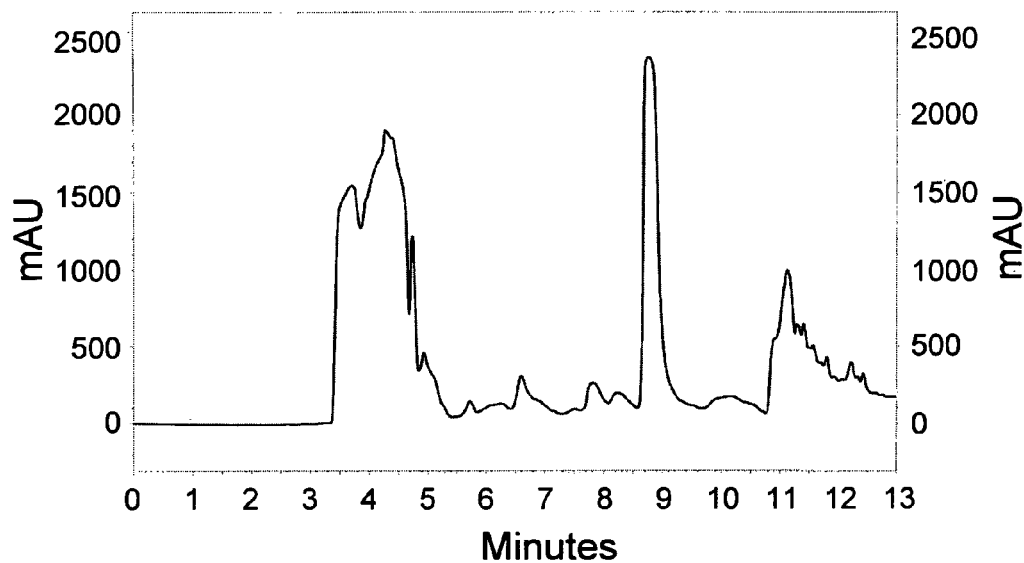
FIG. 1A is HPLC chromatogram of extracted metabolites from *Meira argovae*.
Figure 1B:
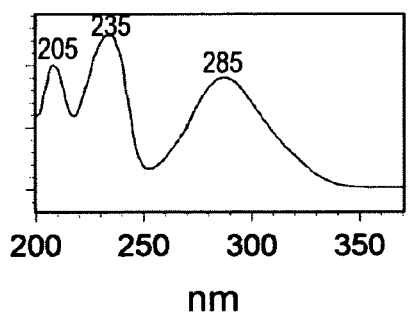
FIG. 1B is a UV Spectrum related to the second major peak, of which elution starts at 8.46 min.
Figure 1C:
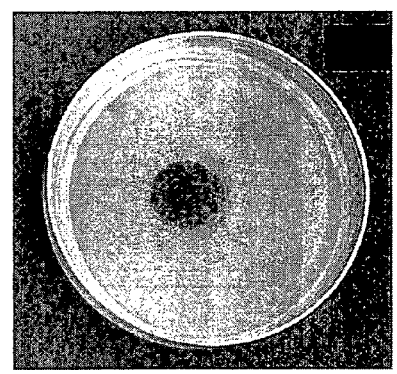
FIG. 1C shows applying the material eluted in said second major peak as the bioactive toxin inhibiting the growth of *Agrobacterium tumefaciens*.
Figure 2:
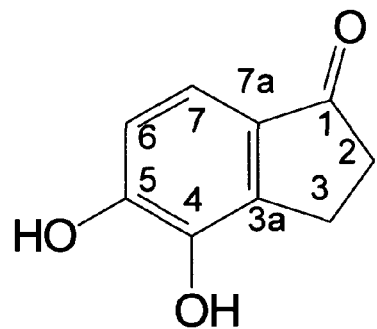
FIG. 2. shows the proposed structure of the active agent, called argovin herein, namely 4,5-dihydroxyindan-1-one (molecular formula, $C_9H_7O_3$), being a mite-antagonistic compound secreted by *Meira argovae*.

The invention thus relates to a pesticidal formulation comprising a component derived from a fungal extract. Particularly, *Meira argovae* fungus was employed; the crude fungal extract was then chromatographed and bio-assayed. Three major peaks, detected by the RPLC analysis (FIG. 1A), were collected and used for bioassays, along with other non-UV detected fractions that had eluted from the RPLC. Only one peak, eluted at 8.46 min, whose UV spectrum was characterized by λmax=205, 235 and 285 nm (FIG. 1B), was active against *A. tumefaciens* (FIG. 1C). The fraction characterized by λmax=205, 235 and 285 nm was collected, lyophilized and subjected to analysis by MS and MS/MS and by different modifications of the NMR spectroscopy. M-H mass of the compound was 163.0401 (molecular formula, C9H7O3). According to the MS/MS spectrum, the major losses of the M-H peak are H2, H2O, CO and CH2=C=O. The $^1$H-NMR spectrum of the compound in CD3OD solution shows four groups of protons: multiplet at δ=2.66 (2H), multiplet at δ=3.04 (2H), doublet at δ=6.86 (1H, J=8 Hz) and doublet at δ=7.17 (1H, J=8 Hz). The 13C-NMR spectrum shows 9 different signals at δ: 23.18 (CH2 according to DEPT spectra), 37.45 (CH2 according to DEPT spectra), 116.76 (CH according to DEPT spectra), 117.09 (CH according to DEPT spectra), 130.69, 142.92, 144.58, 152.89, 208.99. The HQMC spectrum allowed us to assign the protons with δ=2.66 to carbon atom with δ=37.45, protons with δ=3.04 to carbon atom with δ=23.18, proton with δ=6.86 to carbon atom with δ=116.76 proton with δ=7.17 to carbon atom with δ=117.09. Evidently, the carbon with δ=208.99 belongs to a carbonyl group. According to the COSY spectra, the two CH2 groups are linked to each other, and the same holds for the two CH-groups. All the above presented data lead us to the suggestion that the analyzed compound has an indan-1-one skeleton with two hydroxyl groups linked to aromatic moiety. The HMBC spectrum i) H(2.66) was found to be in interaction with C(23.18, strong), C(130.69, weak), C(144.58, strong), C(208.99, strong); ii) H(3.04) was in interaction with C(37.45, strong), C(130.69, strong), C(142.92, strong), C(144.58, strong), C(152.89, strong), C(208.99, strong); iii) H(6.86) was found to be in interaction with C(130.69, strong), C(142.92, strong), C(152.89, weak); iv) H(7.17) was found to be in interaction with C(144.58, strong), C(152.89, weak), C(208.99, strong). With the following assignment of the NMR signals: 23.18 (23.54)-C(2), 37.45 (37.20)-(C3), 116.76 (115.07)-(C6), 117.09 (119.01)-(C7), 130.69 (128.89)-(C7a), 142.92 (142.23)-(C4), 144.58 (142.93)-(C3a), 152.89 (152.29)—(C5), 208.99-(C1). The assignment was supported by good agreement between the measured and calculated $^{13}$C chemical shifts (shown in the parentheses), the calculations were performed using the ACD (version 10.0) $^{13}$C-Predictor during the visit of second author in the laboratory of Prof. G. Gescheidt, Graz (University of Technology, Graz, Austria). The additional data suggest that the analyzed compound structure is 4,5-dihydroxyindan-1-one (syn. 4,5-dihydroxy-1-indanone; 4,5-dihydroxy-2,3-dihydro-1H-inden-1-one) and was consequently named argovin (FIG. 2). The major metabolite of the toxic fraction was thus identified.

Figure 3:
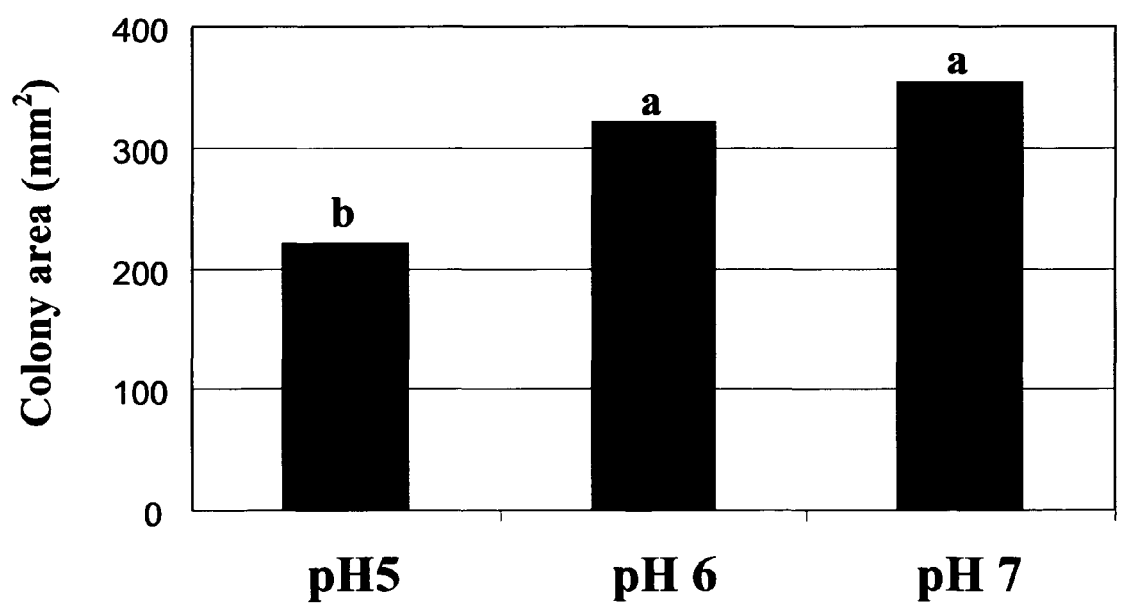
FIG. 3. is a graph showing colony areas of *Meira argovae* colonies grown on phosphate buffered media, with initial pH values of 5, 6, or 7; different letters denote significant differences between the treatments (at $p<0.05$)
Figure 4:
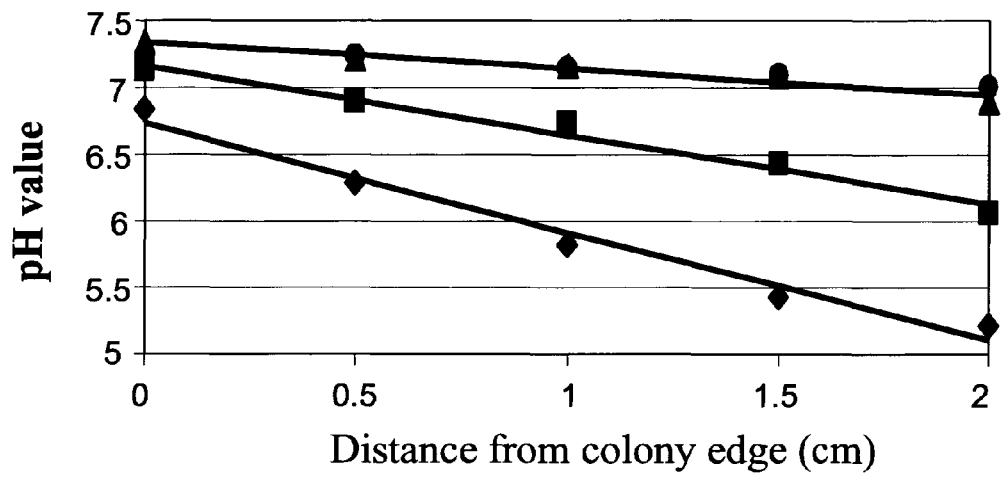
FIG. 4. is a graph showing the pH changes induced by *Meira argovae* colony in non-buffered media; initial pH of media was 4.0 (♦), 4.5 (■), 5.0 (▲) or 6.0 (●), respectively; the pH changes were monitored by readings at equal distances from the colonies edges.
Figure 5:
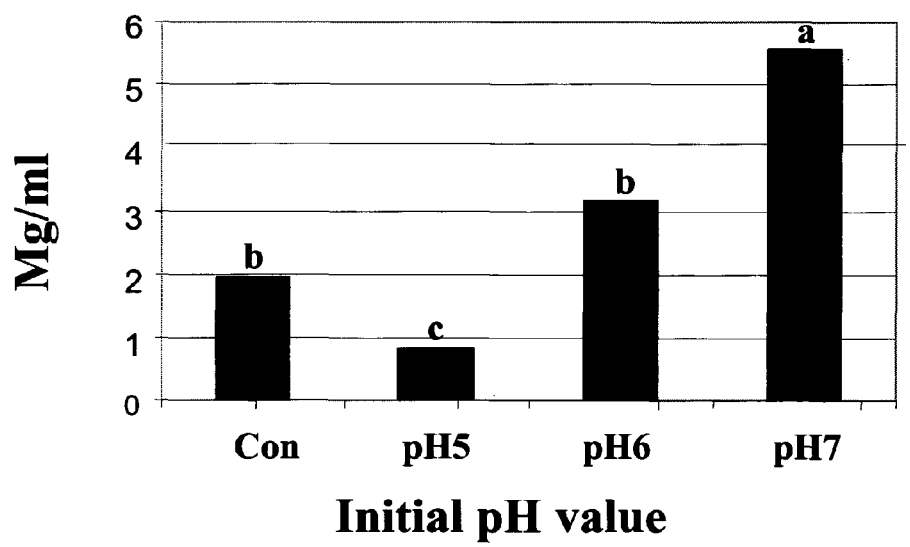
FIG. 5. is a graph showing pH-dependent toxin production by *Meira argovae*, as detected by HPLC; the fungus was grown in liquid phosphate-buffered media, with initial pH values of 5, 6, or 7, or control (Con), which is a non-buffered medium (initial pH of 5.0); different letters denote significant differences between treatment (at $p<0.05$)

The effect of different pH values on fungal growth was examined. Fastest fungal growth took place on media buffered to pH 6.0 and 7.0 (attaining an average of 311 mm$^2$ and 327 mm$^2$ in diameter, respectively), as compared to 222 mm$^2$ at pH 5.0 (FIG. 3). Measuring changes in the pH values (InLab® 427 microelectrode) in the growth media indicated higher values near the colonies' edges, as compared to other sites. The initial pH of the media, which came to 4.0, rose to 6.0 after 21 days (measured at 20 mm from the colonies' edge). When the initial pH values were 4.5, 5.0 or 6.0, they ascended to 7.2, 7.3 and 7.3, respectively (FIG. 4). Further, the effect of pH values on the quantity of argovin secretions was characterized. The highest amount of toxin secretion was measured in colonies grown at pH 7.0 (5.2 mg/ml) buffered media, as compared to that obtained when the fungus was grown at pH 6.0 (3.1 mg/ml) or at pH 5.0 (0.98 mg/ml). The amount of secretions in the non-buffered control was not statistically different (1.99 mg/ml) from that obtained at pH 6.0. The pH in the non-buffered controls rose during the experiment from 5.0 to 6.0 (FIG. 5).

Figures 6, 7:
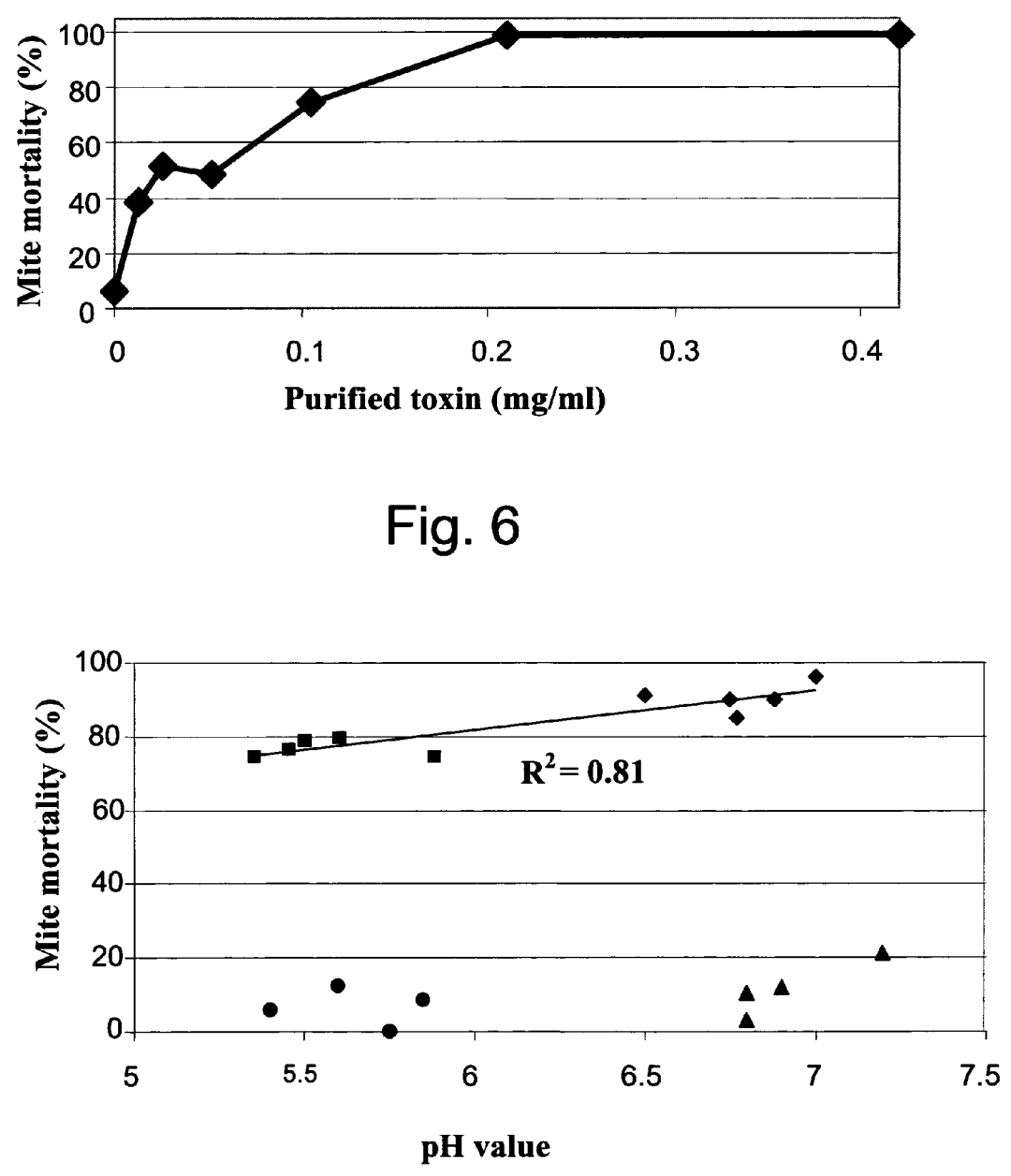

The effect of the changing pH of grapefruit peel on the antagonism of *M. argovae* to the citrus rust mite was checked. The pH value of non-ripe grapefruit peels was close to 5.5, and that of ripe fruits, 6.5. Following the application of fungal conidia, highest mite mortality (85%) was seen on ripe fruits, as compared to 78% mortality (significantly different at 0.05) on non-ripe fruits. In the control treatment (water only), which included CRM on ripe or non-ripe fruits, mortality came only to 11 and 9%, respectively. These data suggest an association between the peel's pH level and mite mortality ($R2=0.81$) (FIG. 7).

The dose response of the citrus rust mite to argovin concentrations was measured. The active fraction (at 0.01 mg/ml) caused 39% mortality (vs. 6% in the control), rising to 100% mortality at 0.2 mg/ml (FIG. 6).

The present invention thus provides the means to fight the pests, such as *A. tumefaciens* and the citrus rust mite (CRM), by employing a compound secreted by *Meira argovae*. An RPLC method is provided for detecting and isolating the bioactive fraction in the fungal secretions, particularly wherein the fungus comprises *M. argovae*. The provided bioassay is very practical because the utilization of *A. tumefaciens* allows the overnight reading of the results. The identification and characterization of the fungal substance 4,5- dihydroxyindan-1-one (termed here argovin) was enabled, the substance being toxic to *A. tumefaciens* and to the CRM.

No report has been found by the inventors about secreting the compound argovin by any organism, nor about its biological activity. Singh et al. (1989) described this compound as an intermediate between 4,5-dimethoxyindan-1-one and 4,5-dibenzyloxy-2,3-dihydro-1-H-indaen-1-one, in a study aimed at understanding the stereochemical assignments of these compounds, without relating to biological activities. A similar compound, 5,6-dihydroxyindan-1-one, was reported as an intermediate in the bromination of 5,6-dimetoxyindan-1-one bromination, without relating to any biological activity (Choi and Ma, 2007). Different derivatives of 1-indanone were reported to have an adverse effect on breast cancer growth in human cells in vitro (Somers-Edgar and Rosengren, 2009). According to another study, derivatives of 1-indanone have pharmaceutical uses against Alzheimer's disease (da Silva et al., 2006).

Many fungi that served as biocontrol agents (or potential biocontrol agents) secrete toxic secondary metabolites that are the main, or the only, mode of antagonistic activity (Vey et al., 2001). For example, the yeast-like fungus *Pseudozyma flocculosa*, a species related to *Meira argovae*, is a potential biocontrol agent that secrets toxic fatty acids (Avis and Belanger, 2001) and a cellobiose lipid (Cheng et al., 2003), which were verified as the main modes of action against cucumber powdery mildew and *Phomopsis* sp. (Avis and Bélanger, 2001; Cheng et al., 2003).

Changes in pH values also affect growth rates in other fungal systems. For instance, *Coniothyrium minitans*, a mycoparasite of *Sclerotinia* spp., grows better and produces more toxins under acidic than neutral-alkali conditions (Yang et al., 2008). The entomopathogenic fungus *Metarhizium anisopliae* regulates the ambient pH, which activates its cuticle-degrading enzymes and amplifies a toxic secretion following penetration (St Leger et al., 1999). In the instant case, it seems that the changes in the pH of the grapefruit peel during ripening contributes to fungal development and allows argonin secretion to occur at a higher rate. In this work, it is demonstrated that *M. argovae* changes the pH of its environment to neutral when grown on artificial media, and as a result secretes higher amounts of argovin, as compared to more acidic conditions. Argovin directly causes mite death, as shown by its enhanced mortality upon increasing the amounts of toxin applied. The fact that argovin is capable of inhibiting *A. tumefaciens* as well as mites (e.g. prokaryote and eukaryote organisms) suggests that it may have pharmaceutical along with agricultural uses. Little information is available on fungal mycotoxins, especially those of the *Ustilaginomycetidae* (Vey et al., 2001), to which *M. argovae* belongs. This fungus is shown as having a great potential of becoming a biocontrol agent against herbivorous mites and other plant pathogens, including fungi and bacteria. The link between grapefruit peel pH and the antagonistic activity of the fungus can be manipulated when using it against citrus mites. Applying the fungus in an alkali medium/formulation may lead to higher pest mortality, regardless of the environmental pH. This biological trait may also be exploited in order to obtain more argovin when producing it for industrial and pharmaceutical purposes. This work identifies and characterizes the toxic secretion of *M. argovae* and its dependence on the ambient pH. For the first time, argovin is described as a living organism metabolite (fungal), beside demonstrating its effects in reducing pest-mite populations.

In a preferred embodiment of the present invention, the formulation is used in protecting the crops against mites, fungi and/or bacteria, the formulation comprising a fungal extract or a component isolated from such extract, particularly an extract from *M. argovae*. In one embodiment, said isolated component is derivatized by known chemical processes. Preferably, a fungal extract or its component is applied onto plants to be protected or in their vicinity, the extract comprising 4,5-dihydroxyindan-1-one or a derivative thereof. Said derivative may comprise an ester or ether. Particularly, derivatives that are easily hydrolyzed in the pest bodies to provide free 4,5-dihydroxyindan-1-one are preferred.

Provided is a pesticidal formulation comprising 4,5-dihydroxyindan-1-one and agriculturally acceptable carriers, auxiliaries or diluents, such as solvents, emulsifiers and dispersants or surfactants. In some embodiments, the formulation of the invention may comprise another pesticide providing a synergistic effect against mites, fungi and/or bacteria, or providing activity against additional pests. For some uses, the formulation may further contain active ingredients, such as herbicides, insecticides, growth stimulators, and fertilizers.

In yet another aspect of the invention, a method for controlling and/or preventing infestation by mites, fungi and bacteria in agriculturally important plants is provided. In one embodiment of the invention, a method for controlling and/or preventing infestation by mites, fungi and/or bacteria in agriculturally important plants is provided.

For the purpose of carrying out the invention, the acaricidal, fungicidal and bactericidal suspension or solution can be applied by any way known in the art of pesticide use and agricultural protection.

The invention will be further described and illustrated in the following examples.

EXAMPLES

Fungal and Bacterial Strains, Growth Conditions and Crude Fungal Metabolite Extraction

*Meira argovae* (strain AS005, Boekhout et al., 2003) was employed. The fungus was routinely grown on potato dextrose agar (PDA, Difco, Detroit) at 25° C., and maintained at 4° C. until used. For metabolite extraction, the fungus was grown in 30 ml yeast malt peptone dextrose (YMPD) broth (Cheng et al., 2003) for 28 days in the dark, with constant agitation (150 rpm). Extraction of metabolites followed Duffy and Defago (1999), with minor changes as described previously (Paz et al., 2007b). A culture of *Agrobacterium tumefaciens* (strain ID1) used for the bioassays, was kindly provided by Prof. Leonid Chemin of the Hebrew University of Jerusalem.

Source of the Citrus Rust Mites

The CRM population was obtained from Mineola Tangelo (*C. paradisi*×*C. reticulata*) fruits at the Tzrifin farm, on the coastal plain of Israel. No acaricides are being used at this farm, making the location a suitable place for our purposes. In the laboratory the pest was reared on young seedlings (6-8 weeks old) of sour orange (*Citrus aurantium*).

Crude Extract Chromatography

Reversed phase liquid chromatography (RPLC) separation was performed to detect biologically active fractions from the crude fungal extract. The HPLC system (Thermo Separation Products, Riviera Beach, Fla.) consisted of an auto-sampler (AS3000), injector (100 µl), column oven (35° C.), pump (P3000) and diode array detector (UV6000). A reverse phase C18 column (250×4.6 mm, "Luna" 5µ Phenomenex, Torrance, Calif.) was employed. Elution was performed using a linear gradient consisting of double distilled water (ddH2O) and acetonitrile, initially an isocratic step was employed for 3 min at 85% water, followed by a moderate increase in acetonitrile to reach 17% in 14 min, at a flow rate of 1 ml/min. The crude extract was monitored at λmax=210, 232 and 285 nm. Each of the detected fractions was collected and bio-assayed (see below).

Assay of Antibacterial Activity and Crude Extract Effect on the Citrus Rust Mite The crude extract was initially assayed in vitro against *A. tumefaciens*, because preliminary results had indicated that this bacterium is sensitive to the extract and therefore suitable for our bioassays. The bacterium was grown overnight in glass tubes containing a 5 ml Lennox Broth (LB, Difco). Fifty μl overnight-grown bacterial suspensions were added to 5 ml of LB containing 0.6% agar, and placed into Petri dishes (55 mm diameter). Each of the eluted chromatographed fractions was dried using a rotor evaporator, dissolved in 10 μl of methanol, pipetted into the Petri dishes and incubated at 28° C. Each dish was checked for inhibition haloes 24 hours later; 10 μl methanol alone was used as a control. This procedure was repeated four times to confirm of the toxicity of the fractions. The RPLC-cleaned fraction that was antagonistic to *A. tumefaciens* was concurrently assayed against the citrus rust mite (describe below).

MS and NMR Analysis of the Toxic Fraction

MS analysis was performed on a Bruker Daltonik micrOTOF-Q mass spectrometer equipped with an ESI ion source. The following MS parameters were used for the analysis: capillary voltage 4000 V, nebulizer pressure 0.6 Bar, dry gas flow 5 l/min, dry gas temperature 180° C., ISCID energy 1 eV/z, ion energy 3 eV/z, collision energy 10-40 eV/z, mass range 100-2500 Da. Samples were analyzed in positive and negative mode; better results were obtained by the latter. A Bruker "Avance" DRX-500 NMR spectrometer, operating at 500 MHz for 1H and at 125 MHz for 13C, was used for the NMR experiments; chemical shifts are expressed in δ (parts per million) referring to the solvent peaks $δ_H$ 3.34 and $δ_X$ 49.0 for CD3OD; coupling constants, J, are in Hz.DEPT, 1H-1H COSY, 1H-13C HSQC, and HMBC NMR experiments were carried out using the conventional pulse sequences as described in the literature.

The Effect of Different pH Values on Fungal Growth

In order to assess whether colony growth is affected by ambient pH, a six mm plaque from the edge of a fungal colony (on PDA) was placed in the center of 90 mm Petri dishes containing buffered YMPD with 2% agar (The buffer solution (citrate/phosphate) contained 0.1 M citric acid and its pH was adjusted to the levels of 5.0, 6.0 or 7.0 by adding amounts of 0.2 M Na2HPO4, as needed.). These Petri dishes (5 replicates) were incubated for 21 days at 25° C. in the dark. The diameter of each colony was measured in order to obtain its growth area. Alizarin S red dye (Sigma) (0.2%) was added onto each dish before colony measurement; this dye is known to signal changes in acidity by forming a red halo when the pH rises above 5.8. The actual pH values were measured by a pH meter, with an InLab® 427 microelectrode at equal distances (5 mm) from the colonies edges. The fungus was also grown for 21 days at 25° C. in a non-buffered YMPD (2% agar) medium, whose pH values were adjusted to 4.0, 4.5, 5.0 or 6.0. The pH values were recorded at increasing distances from the colonies' edges (0.5, 1.0, 1.5 and 2.0 cm).

Effect of pH Values on the Quantity of Toxic Secretions

The purpose of this experiment was to determine the effect of the pH of the media on toxin secretions and to establish the optimal pH conditions for the secretion. A suspension of three ml ($1 \times 10^8$ spores/ml) in ddH2O was added to 30 ml buffered (phosphate/citrate, as above) YMPD in Erlenmeyer flasks. The flasks were constantly agitated (150 rpm) for five days in the dark. Non-buffered YMPD media served as controls. The amounts of the extracted toxic metabolite resulting from each pH treatment were measured with the RPLC system.

The Dose Response of the Citrus Rust Mite to Purified Toxin Concentrations

In order to determine the CRM dose response to the toxin, 0.01, 0.02, 0.05, 0.1, 0.2 and 0.4 mg/ml of RPLC-cleaned toxin, dissolved in a two ml volume of ddH2O, was sprayed on the CRM (thirty CRMs/leaf, in four replicates). The infested seedlings were incubated at 25° C., (12L: 12D). Mite mortality rates were recorded 24 h later.

The Effect of the Changing pH of Grapefruit Peel on the Antagonism of *M. Argovae* to the Citrus Rest Mite This experiment was conducted in order to explore the effect of the pH of grapefruit peels on the fungal antagonism against the CRM. Ten ripe and ten non-ripe red grapefruits (*Citrus paradisi* cv. Star Ruby) were collected at Tzrifin farm, as above, and the mites were from young seedlings, as noted. The pH of the fruits' outer peel layer was measured, as above, with an InLab® 427 microelectrode (Mettler Toledo, Schwerzenbach, Switzerland). Each grapefruit was infested by about 30 mites. Treatments included the spray of a fungal suspension (1×108) on 5 ripe and 5 non-ripe infested fruits and a water treated control, also on 5 ripe and 5 non-ripe fruits. CRM mortality was recorded five days post-treatment (at 25° C., 12L:12D; light:dark).

Statistical Analysis

Each experiment was conducted twice with 3-5 replicates. Data obtained were analyzed by ANOVA Tukey's test (P=0.05) using JMP 8.0 Software (SAS Institute, Cary, N.C.). For the mite-infested red grapefruits experiment, a regression analysis was conducted.

The Effect of Three Basidiomycotine Fungi on Soil-Borne, Foliage and Fruit-Damaging Phytopathogens The effect of three basidiomycotine fungi, *Meira geulakonigii, Meira argovae* and *Acaromyces ingoldii* on seven phytopathogenic fungi, *Colletotrichum gloeosporioides, Fusarium mangiferae, Pencillium digitatum, Phytophthora citrophthora, Rhizoctonia solani, Sclerotinia sclerotiorum* and *Sclerotium rolfsii* was assayed in the laboratory. The phytopathogens fungi were placed on dialysis membranes covering media on which the basidiomycotine fungi had formerly been cultured, thus exposing them to the extracts of the latter. *Acaromyces ingoldii* inhibited the growth of all phytopathogens fungi, whereas the *Meira* spp. hindered these fungi to variable extents. Upon being returned to extract-free media, all phytopathogenic fungi resumed growth, suggesting that the inhibitory effect of the basidiomycotine fungi is fungistatic. The three basidiomycotine fungi inhibited the growth of *S. sclerotiorum* on tomato leaves for a few days and *Meira* spp. totally hindered the infection of oranges by *P. digitatum*, whereas *A. ingoldii* was less effective. Results of preliminary assays suggest that neither competition for hydrocarbons nor secreted proteases are responsible for the inhibitory activity of the basidiomycotine fungi, whereas micro-molecules may play a part.

Interest in the biological control of phytopathogenic fungi with microorganisms, including fungi, has increased in recent years. We recently discovered several indigenous fungi that were assigned to the Exobasidiomycetidae of the Ustilaginomycetes (Basidiomycota), and described as new taxa by Boekhout, Theelen, Houbraken, Robert, Scorzetti, Gafni, Gerson, and Sztejnberg (2003). Although the fungi were obtained from cadavers of pestiferous mites, we assayed one of these species, *Meira geulakonigii* Boekhout, Gerson, Scorzetti & Sztejnberg, against a powdery mildew. The rationale for this assay was the close phylogenetic relationship of the genus *Meira* to *Pseudozyma* Bandoni emend. Boekhout, one of whose species, *Pseudozyma flocculosa* (Traquair, L. A. Shaw and Jarvis) Boekhout & Traquair, is known as an antagonist of powdery mildews. The target disease was cucumber powdery mildew, caused by *Sphaerotheca fusca* (Fr.) Blumer, affecting cucumber. We found that leaf coverage of the powdery mildew was significantly reduced and cucumber fruit yield was significantly increased after being treated with blastoconodia of *M. geulakonigii* (Sztejnberg, Paz, Boekhout, Gafni, and Gerson 2004). Later we reported that *M. geulakonigii* and the other new species, *Meira argovae* Boekhout, Gerson, Scorzetti & Sztejnberg and *Acaromyces ingoldii* Boekhout, Gerson, Scorzetti & Sztejnberg, also inhibited two soil-borne phytopathogenic fungi, *Sclerotinia sclerotiorum* (Lib.) de Bary and *Sclerotium rolfsii* (Sacc.) (Gerson, Paz, Kushnir, and Sztejnberg 2005). We formerly postulated that as neither *Meira* spp. nor *A. ingoldii* are parasitic (Sztejnberg, Paz, Boekhout, Gafni, and Gerson 2004), their antagonistic effect on mites and fungi is due to excreted toxins. This hypothesis was confirmed upon exposing sclerotia of *S. sclerotiorum* and *S. rolfsii* to crude extracts (e.g. devoid of fungal matter) of all three fungi, and obtaining significant inhibition of the growth of emerging mycelia (Gerson Paz, Kushnir, and Sztejnberg 2005). In a later study (Paz, Burdman, Gerson, and Sztejnberg 2007b) we found that, the crude extract of *M. geulakonigii* secretions caused 100% mortality of a mite pest. Herein we present data on the impact of these three fungal biocontrol agents (FBAs) on phytopathogenic soil-borne fungi; we add data about the effects of the secretions crude extract, from the FBAs on *S. sclerotiorum* and *S. rolfsii*, as well as on *Rhizoctonia solani* (Kuehn), the causative agent of root rot diseases. We also describe the effects of the FBAs on pestiferous leaf- and fruit-damaging fungi. These are: *Colletotrichum gloeosporioides* (Penz.) Penz. & Sacc.; *Fusarium mangiferae* Britz, Wingfield & Marasas; *Pencillium digitatum* Sacc. and *Phytophthora citrophthora* (Sm. & Sm.) Leonian.

Source and Culture of the Beneficial Fungi

Details of the provenance of the FBAs are in Boekhout, Theelen, Houbraken, Robert, Scorzetti, Gafni, Gerson, and Sztejnberg (2003). Suffice to note that *M. argovae* (isolate AS005) was obtained from cadavers of the two-spotted spider mite (*Tetranychus urticae* Koch), *M. geulakonigii* (isolate AS004) from dead citrus rust mites (*Phyllocoptruta oleiuora* Ashmead), and *A. ingoldii* (isolate AS001) was from the same mites at another site. All isolates were routinely grown in the dark on 3.9% w/v potato dextrose agar, amended with 250 ppm chloramphenicol (PDAC) at 25° C., in Petri dishes (9 cm diam).

*Meira argovae* and *M. geulakonigii* were also grown within Erlenmeyer flasks on the liquid medium potato dextrose broth (PDB), but *A. ingoldii* (which does not form blastoconidia in liquid media) was maintained on PDAC. Blastoconidia suspensions were obtained by centrifuging (4,000 RPM) the contents of the flasks, pouring out the supernatant and re-hydrating the blastoconidia-containing residue with 50 cc deionized water ($_dH_2O$). The concentration of the blastoconidia was then established by counting with a h hemocytometer. Similar amounts of the blastoconidia of *A. ingoldii* were obtained by adding five cc of $_dH_2O$ to the Petri dishes in which that fungus had developed and repeating the same procedure.

Source and Culture of the Phytopathogenic Fungi and Chromista

A culture of *S. sclerotiorum*, which infects many commercial crops, was obtained from Prof. O. Yarden of our university, from the culture collection of the Department of Plant Pathology and Microbiology at the Hebrew University of Jerusalem, Israel. This fungus secretes oxalic acid that damage plants and forms sclerotia that may survive in the soil for long periods (Agrios 2005). Cultures of *S. rolfsii* and of *R. solani*, both of which also infect many crops, were obtained from Prof. Y. Katan, also of our university; these fungi also form sclerotia. They were maintained on PDAC. Prior to exposing them to the various crude extracts they were grown on DWA (deionized water agar) at their preferred temperatures (*S. sclerotiorum* at 19° C., *S. rolfsii* and of *R. solani* at 29° C.). Sclerotia of the fungi were obtained by letting their cultures dry up and then harvesting the dried sclerotia. Cultures of *C. gloeosporioides* and of *F. mangiferae* were obtained from Dr. S. Freeman, Volcani Institute, Bet Dagan, Israel. The culture of *P. digitatum* was received from Dr. S. Droby at the same institute, and that of *P. citrophthora* from our lab culture collection. *Colletotrichum gloeosporioides* damages many field crops as well as citrus and avocado, whereas *F. mangiferae* is the causative agent of mango malformation disease. *Pencillium digitatum* causes the green mould that damages picked citrus fruit (e.g. a post-harvest disease), and *P. citrophthora* affects the citrus by causing food rot, gummosis and fruit brown rot. All fungi cultured like the FBAs. Prior to exposing them to the various extracts they were transferred from PDA to DWA (in order to avoid the residual effects of nutrients that could interfere with extract effects) and incubated at 25° C.

Short-term, non-replicated observations were also conducted on two additional pathogenic fungi, namely *Alternaria alternata* (Fr.) Keissl, obtained from our University, and *Botrytis cinerea* (De Bary) Whetzel from Dr. Y. Elad, Volcani Institute, Bet Dagan, Israel. The former causes leaf spots on many commercial plants, whereas the latter causes grey mould on grape, strawberry and various vegetables crops. They were cultured as above.

Experimental Set-Up

In order to eliminate any accidental contact between the FBAs and the pathogens, discs (18 mm diam) of each of the former, taken from one-week old colonies, were transferred onto membranes cut from dialysis tubing 12-kDa cutoff (Visking dialysis membrane, 12 kDa, Medicell International LTD, London, UK) placed on PDAC in Petri dishes. The area of the membranes was larger than the dishes, covering the medium as well as the inner walls of the dishes, in order to avoid any contact between media and fungi. These membranes are known to allow the diffusion of micro-molecules but not of macro-molecules or enzymes. The dishes were incubated at 25° C. for 10 days, the membranes with the FBAs then being removed, leaving the media with the extracts of each FBA without any residues of their mycelia or blastoconidia ("extract dishes" hereinafter). Discs (eight mm diam) of the pathogen cultures (including the two "short-term" fungi), which had been maintained on DWA, were then placed in the center of the extract dishes.

Most cultures (except *S. sclerotiorum* at 19° C., *S. rolfsii* and of *R. solani* at 29° C.) were kept at 25° C. and their mycelial growth was measured every 24 hrs; the obtained data were used for estimating colony growth. Each pathogen-FBA combination was replicated eight times, in two series. Control dishes (with PDAC only) were inoculated with the same pathogens and similarly examined. After recording the effects of the extract, all pathogen-bearing discs were placed onto PDAC plates without any FBA extracts. This was done in order to observe any further fungal growth and thus determine whether the extract effects were fungicidal or fungistatic.

The amount of conidia or sclerotia produced by each pathogen (except *P. citrophthora*, a species that produces zoospores, which cannot be assayed by this method) was estimated by adding five cc of $_dH_2O$ to each plate, pouring the obtained suspense into an Eppendorf tube and then counting with a hemacytometer. Number of replicates was as above.

Germination and Production of Pathogen Sclerotia and Conidia

The effect of the FBAs on the germination and mycelial growth from dried sclerotia was assayed by placing 20 sclerotia of *S. rolfsii* and 20 of *S. sclerotiorum* on the extract dishes obtained from each FBA (*R. solani* did not form sclerotia in our cultures), and measuring colony growth, as above. The dishes with *S. rolfsii* were kept at 29° C., those of *S. sclerotiorum* at 19° C., and extent of germination was assessed after two days. Production of sclerotia by *S. rolfsii* and by *S. sclerotiorum* in the pathogen cultures kept on the extract dishes was monitored after 15 and 10 days, respectively. Due to the fact that *S. sclerotiorum* produced no sclerotia (see below), only the sclerotia of *S. rolfsii* were tested for viability by placing them on filter paper impregnated with bromo cresol blue, which changes its color to dark-yellow as the sclerotia germinate (Gamliel, Grinstein, Klein, Cohen, and Katan 1998).

Suspensions of conidia ($10^8$ ml$^{-1}$) in $_dH_2O$ of *C. gloeosporioides, F. mangiferae* and *P. digitatum* were placed on the extract dishes of the FBAs and incubated at 25° C., the former two for one week, *P. digitatum* only during four days. At the end of these periods, the number of germinating conidia (whose germ tubes exceeded the length of the pertinent conidium) was counted in four microscopic fields per dish, averaged and percent of germination was calculated. Each pathogen-FBA combination was replicated four times, in two series. Control dishes were prepared and examined as above.

In addition, discs with the conidia of *P. digitatum*, which did not germinate at all (see below), were transferred onto PDAC dishes devoid of any fungal extracts, in order to determine the duration of the inhibition, as above.

Inhibition of *Sclerotinia sclerotiorum* by the Beneficial Fungi on Tomato Leaves Young tomato leaflets, placed on humid filter paper in Petri dishes, were sprayed with 1-5×$10^8$ ml$^{-1}$ suspensions of the blastoconidia of each of the FBAs in $_dH_2O$; control leaves were treated with water only. The closed dishes were kept for 10 days at 19° C., after which discs (2 mm diam) taken from the middle of a *S. sclerotiorum* culture were placed on each leaflet. The dishes were returned to 19° C. Mycelial growth on the leaves was measured every 24 hrs (until the control leaves became covered by the pathogen), and the obtained data were used for estimating the extent of FBA inhibition. Each FBA was assayed twice, each time on 5-8 leaflets, in 5 replicates.

Tomato leaves treated with the FBA and then with *S. sclerotiorum* were examined by a scanning electron microscope (SEM) as previously described (Paz, Burdman, Gerson, and Sztejnberg 2007b). In short, samples were immersed in glutaraldehyde (5%) for two hours, washed thoroughly with buffer phosphate (pH 7.2), dried and gold-plated. They were then examined by a JSM 5410 scanning electron microscope (Jeol Ltd, Tokyo, Japan), in high vacuum mode, in order to examine the actual interactions between the FBAs and the pathogen on the leaves.

Inhibition of Citrus Green Mould of Oranges by the Beneficial Fungi

Sweet oranges (*Citrus sinensis* cv. New Hall) picked from an organic orchard near Rehovot were surface sterilized with 90% ethanol. FBA blastoconidia were obtained as above, and a suspension ($10^8$ ml$^{-1}$) of each was sprayed onto the oranges, which were then kept in a sterile humid chamber at 25° C. for 10 days. At that time a small wound (2 mm length and depth) was scratched on its peel by a sterilized instrument, and 50 ml of the *P. digitatum* conidial suspension (5×$10^3$ ml$^{-1}$) was smeared on each wound. Each FBA was applied onto 10 oranges (in two series of five each), which were kept, along with suitable controls (wounded but untreated with FBAs) at 25° C. for observation. Extent of damage was estimated when the control oranges were completely covered by the mould. Thin cuttings were taken from the oranges that showed green mould inhibition and prepared for SEM examination, as above.

Examining the Mode of Action of the FBAs

Several tests were run in order to obtain preliminary data on the inhibitory mode of action of the FBAs. The tests included determining their rate of hydrocarbon consumption, evaluating the effect of micro-molecules (which are known to traverse the dialysis membrane, in contrast to macro-molecules and enzymes), and determining whether lytic proteases of FBA origin inhibit the pathogens.

Utilization of Hydrocarbons (Sugars)

This test was run to determine whether the inhibitory activities of the FBAs were due to competition for carbohydrates. It was conducted by using the slightly-modified procedure of Poola, Bhuiyan, Ortiz, Savant, Sidhom, Taft, Kirschenbaum, and Kalis (2002). The Anthrone reagent was prepared by adding 70 ml of concentrated sulfuric acid to 30 ml of $_dH_2O$ and then 200 mg Anthrone (Sigma). A standard (or dilution) curve was prepared by placing 0.0, 0.005, 0.01, 0.05 and 0.1 mg glucose to one ml of $_dH_2O$ in glass tubes and adding 5 ml Anthrone to each tube. The tubes were then boiled in a water bath of 100° C. for five minutes, and one ml from each tube glucose concentration was then read at 620 nm by a spectrophotometer in order to obtain a standard curve. Media that had been covered by the dialysis membrane, on which the FBAs had grown, were tested after 10 days. Discs (13 mm diam.) were taken from each FBA (from three different extract dishes) and placed into plastic sealed tubes (13 ml). The media in the tubes were liquidized in boiling water, and samples of 0.1 ml from each tube were diluted in 0.001, 0.005 and 0.01 $_dH_2O$. From each diluted one ml was transferred to a glass tube to which five ml of the Anthrone reagent were added, and maintained for five minutes in a water bath of 100° C. One ml from each sample was transferred to a cuvette and read in a spectrophotometer at 620 nm. Four separate readings were done for each dilution and two separate experiments were conducted for each FBA. The rate of sugar utilization by the FBAs was calculated by comparing the obtained results with data from the dilution curve.

Effect of Proteases Secreted by the FBAs

These tests were conducted to determine whether the inhibitory activities of the FBAs were due to their secreted proteases (Elad and Kapat 1999). The experimental procedure was slightly modified from Kanemitsu, Nishini, Kunishima, Okamura, Takemura, Yamamoto, and Kaku (2001), were conducted in order to determine if lytic proteases of FBA origin, whether in the extract dishes or originating from FBA blastoconidia, participate in pathogen inhibition. The experiments were run in Petri dishes containing five ml gelatin as the substrate. Discs (eight mm diam) from 10-days-old FBA cultures that had been covered by the dialysis membranes were placed in the centre of the gelatin in the dishes and incubated for 7 days at 25° C. Protease activity was determined by adding a 0.1 ml solution of 15% trichloroacetic acid (TCA) to each dish. TCA causes the gelatin becoming murky whereas the broken-down substrate becomes transparent; a clear halo thus forms in the middle of the dishes. Discs from pristine (devoid of FBAs) PDA, and similar discs to which 0.02 ml of proteinase K (Sigma) from a concentration of 0.1 gr/ml dH$_2$O had been added, served as controls, and protease activity was measured as above.

Tests of proteases secretion by blastoconidia of *M. argovae* and *M. geulakonigii* was done in Petri dishes containing five ml gelatin served as substrates. Small wells (3.0 mm depth, 8.0 diam) were bored in the middle of the gelatin in each dish. PDB media on which *M. argovae* and *M. geulakonigii* had developed (as noted, *A. ingoldii* forms no blastoconidia in a liquid medium) were centrifuged for 10 min at 25° C. at 4,000 rpm. A small sample (0.2 ml) from the supernatant (of each FBA), containing the blastoconidia that had not precipitated, was then placed in the wells. Another sample was filtered through a sieve (0.45 micrometer holes) (Schleicher & Schull, London) thus obtaining blastoconidia-free liquid, which was also placed in the gelatin wells. There were two controls: pristine PDB was placed in one group of wells, and proteinase K (0.02 ml) into another. All dishes were incubated for three days at 25° C. and assessed; each FBA was assayed in two series, each with four replicates.

Effect of Micro-Molecules Produced by the FBA.

The purpose of this test was to determine whether the inhibitory activities of the FBAs were due to secreted micromolecules, which could have traversed through the 12 kDa dialysis membrane, or to other compounds, tentatively called toxins. This necessitated a two-stage assay: first applying the heated purified active material on a bacterial colony, and then the heated contents of extract dishes on the pathogenic fungi.

The test bacterium was *Agrobacterium tumefaciens* (strain ID1), obtained from Prof. Leonid Chemin of our University already shown to be susceptible to the FBAs. *Agrobacterium tumefaciens* was grown overnight in tubes containing five ml Lennox Broth (LB) (Difco) undergoing constant shaking at 28° C. A 50-µl aliquot of this bacterial suspension was added to five ml of LB containing 0.6% agar, and placed into small (five mm diam) Petri dishes. Apparent active toxins, obtained from the extract dishes of 10-days' old FBA colonies, were purified using HPLC procedures (Paz 2007) and heated to 100° C. for 15 min. Ten µl of the heated medium from each FBA were then chilled and poured into the middle of the *A. tumefaciens* dishes. Similar amounts of the purified but unheated toxins, as well as unheated media from the extract dishes of each FBA, served as controls. Dishes were incubated at 28° C. for 24 h and observed for any developed inhibition haloes.

The effect of FBA proteins (micro-molecules) secreted into the media was assayed by taking discs (13 mm) from 10 days-old FBA colonies, sealing them in sterile tubes (13 ml), and immediately placing them in boiling water for 15 min, until complete boiling of the media. The boiled media were poured into 5 ml Petri dishes and after solidification DWA discs of one-week old cultures, of either *P. digitatum* or *S. sclerotiorum* were placed at the middle of the dishes. Non-boiled media from the FBAs served as controls. The *P. digitatum* dishes were maintained for three days at 25° C. and those of *S. sclerotiorum* at 19° C. All experiments were repeated twice for each pathogen, in four replicates (tubes).

Statistics Analyses

All obtained data of growth and germination inhibition were analyzed using two-way ANOVA by Dunnett's test (p=0.05), using JMP 5.1.2. Software (SAS Institute, Cary, N.C.). The data were arc-sin transformed prior to analysis. The data obtained from the control treatments were used as reference groups.

Results—Inhibition of Colony Growth and of Conidia Production

These experiments had to be terminated after a few days (3-4 with *R. solani*, *S. rolfsii* and *S. sclerotiorum*, about a week with the other fungi) because the control dishes were totally overrun by the pathogen mycelia. The FBAs inhibited the growth of all pathogens, but the pattern of inhibition differed. Strongest inhibition was obtained in the extracted dishes on which *A. ingoldii* had grown (FIG. 1); only *R. solani* and *F. mangiferae* producing any mycelia thereon. The extracts of *M. argovae* and *M. geulakonigii* also inhibited all pathogens, but to a variable extent. They had a similar inhibitory effect on *P. digitatum* and on *P. citrophthora*, affected *C. gloeosporioides*, *F. mangiferae* (which was totally unaffected by the *M. geulakonigii* extracts) and *R. solani* to different degrees and had a similar effect on *S. sclerotiorum*; *S. rolfsii* appeared to be the least affected.

The short-term observations showed that the extracts of the FBAs also inhibited the growth of the *A. alternata* and *B. cinerea* colonies. The effect on the former was rather mild, similar to that *C. gloeosporioides*, whereas the latter was more strongly affected, like *S. sclerotiorum*.

When the discs with the hitherto-inhibited pathogen cultures were subsequently placed on PDAC without any FBA extracts, all fungi resumed growth and production of conidia.

Inhibition of Sclerotia and Conidia Production

No sclerotia were produced by *S. sclerotiorum* growing on the extract dishes of the three FBAs. *Sclerotium rolfsii*, in contrast, produced a variable number (an average of 39±9.0 on *A. ingoldii*, 87±9.3 on *M. argovae* and 50±5.2 on the *M. geulakonigii* extracts, all significantly less than in the control dishes, which came to an average of 343±19.3). Also, its sclerotia grew only on the dishes' margins and were clearly smaller than those in the controls. The viability (as tested with bromocresol blue) of the *S. rolfsii* sclerotia that had developed on the extracts of the FBAs did not differ from that of the control sclerotia, in all cases coming to nearly 100%.

*Pencillium digitatum* that had developed on the extract dishes of *A. ingoldii* formed no conidia at all, but produced similar amounts (about 5×10$^2$) on the two *Meira* spp. The number of conidia formed by *Fusarium mangiferae* and *C. gloeosporioides* did not differ from the amount produced in the controls (data not shown).

The non-replicated observations on *B. cinerea* showed that this pathogen was inhibited by the FBAs to the same extent as *S. sclerotiorum*. The development of *A. alternata* was hindered to a lesser degree, similar to that seen with *C. gloeosporioides*.

Germination of Sclerotia and of Pathogen Conidia

The germination of the sclerotia of *S. sclerotiorum* and *S. rolfsii* on the various FBAs extracts differed between the two pathogens. The extracts of *M. argovae* and *M. geulakonigii* had no effect on sclerotial germination of the former pathogen, whereas those of *A. ingoldii* totally inhibited germination. However, the germination of the sclerotia of *S. rolfsii* on the extracts of the latter pathogen was affected by their number per dish. None germinated when only one was placed per dish, but 70% and 82% germinated, respectively, when 5 or 20 were put together (Table 1).

TABLE 1

Percent germination of the sclerotia of *Sclerotium rolfsii* on extract dishes on which *Acaromyces ingoldii* (Ai), *Meira argovae* (Ma) and by *Meira geulakonigii* (Mg) had developed.

| No. sclerotia | Ai | Ma | Mg | Control |
|---|---|---|---|---|
| 1 | 0 | 100 | 75 | 100 |
| 5 | 70 | 100 | 100 | 100 |
| 20 | 82 | 100 | 100 | 100 |

Conidial germination of *P. digitatum* was completely inhibited by all three FBAs, whereas *M. argovae* had no effect on *C. gloeosporioides* and on *F. mangiferae*, and *M. geulakonigii* affected only the latter pathogen (Table 2). When conidia of *P. digitatum*, which had hitherto failed to germinate, were placed on the extract-free PDAC, they germinated and formed normal mycelia.

TABLE 2

Percent germination of the conidia of *C. gloeosporioides*, *F. mangiferae* and *P. digitatum* on extract dishes on which *Acaromyces ingoldii* (Ai), *Meira argovae* (Ma) and by *Meira geulakonigii* (Mg) had developed. Asterisk indicates significant differences from the control at $P < 0.05$.

| Pathogen | Ai | Ma | Mg | Control |
|---|---|---|---|---|
| *Colletotrichum gloeosporioides* | 1* | 93 | 92 | 93 |
| *Fusarium mangiferae* | 10* | 90 | 46 | 93 |
| *Pencillium digitatum* | 0 | 0 | 0 | 85 |

Inhibition of Mycelial Growth from the Sclerotia

Figure 9A:
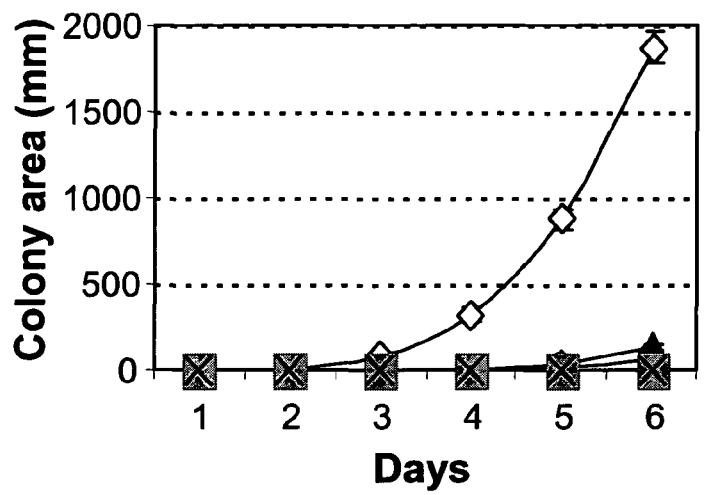
FIG. 9. shows the effect of extracts, prepared from the dishes on which *Acaromyces ingoldii* (Ai), *Meira argovae* (Ma) and *Meira geulakonigii* (Mg) had developed (the symbols are the same as in FIG. 8), on the development of mycelia from the sclerotia of *Sclerotina sclerotiorum* (FIG. 9A) and *Sclerotium rolfsii* (FIG. 9B); the vertical lines indicate SE.
Figure 9B:
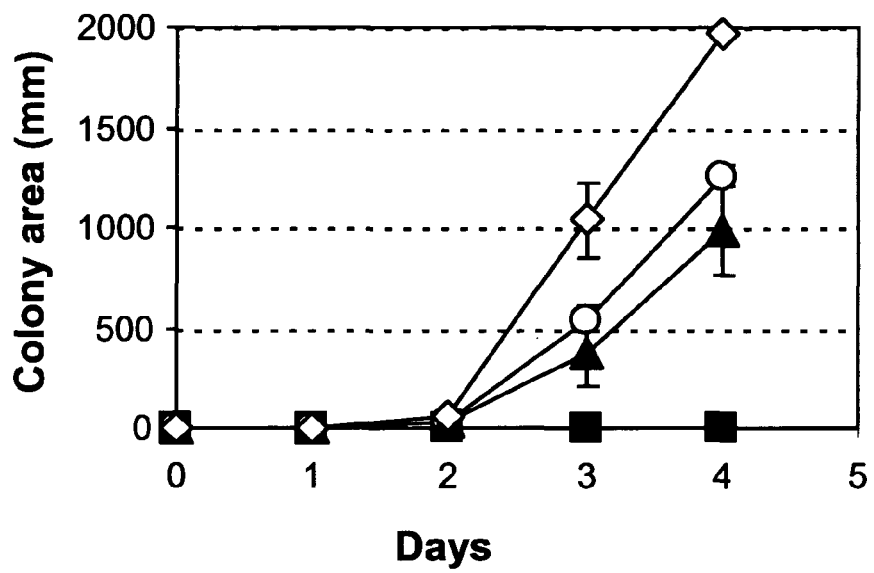

Strongest inhibition was again caused by the extract dishes on which *A. ingoldii* had grown, as no mycelia of *S. sclerotiorum* or of *S. rolfsii* developed thereon. The former pathogen's growth was also almost completely inhibited by the *M. argovae* and the *M. geulakonigii* extracts (FIG. 9A). In contrast, colony growth of *S. rolfsii*, although still significantly less than in the controls (FIG. 9B), was substantial on the *M. argovae* and *M. geulakonigii* extract dishes. The growth pattern of *S. rolfsii* from its sclerotia on the extracts was similar, but slower, to its development from mycelia (FIG. 1).

Inhibition of *S. Sclerotiorum* by the FBAs on Tomato Leaves

Figure 10:
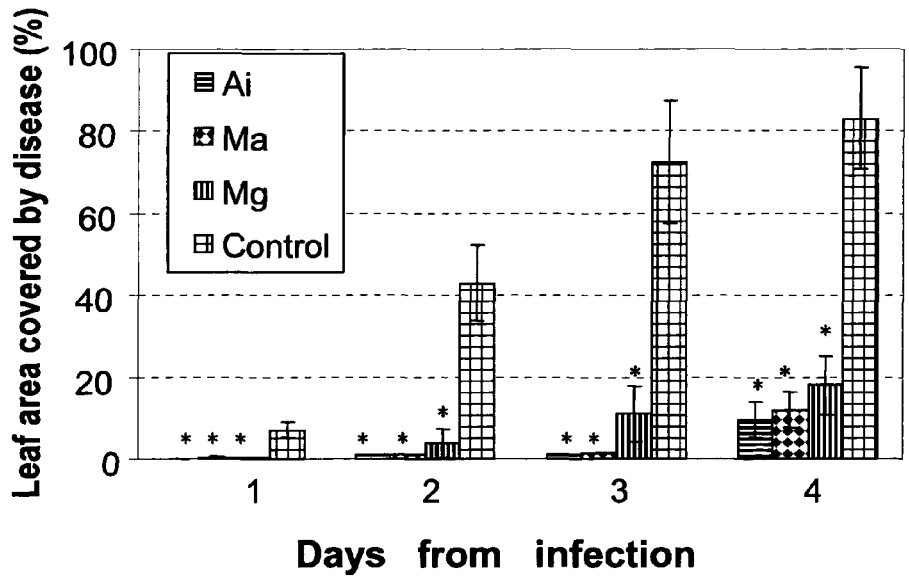
FIG. 10. presents the extent of tomato leaflet coverage by *Sclerotina sclerotiorum* as affected by a spray of $1-5\times10^8$ ml$^{-1}$ suspensions of the blastoconidia of *Acaromyces ingoldii* (Ai), *Meira argovae* (Ma), and *Meira geulakonigii* (Mg) in deionized water; control leaves were treated only with deionized water; the extent of coverage of the control leaflets differed significantly from the effect of all FBAs; the vertical lines indicate SE and the asterisks indicate significant differences from the controls at $P<0.05$.

All FBAs significantly inhibited the growth of *S. sclerotiorum* on the tomato leaflets, albeit to a different extent (FIG. 10). However, by the fourth day the severity of the inhibition declined. Later observations indicated that all leaflets were subsequently overrun by the pathogen (data not shown).

Inhibition of Green Mould Inoculation of Oranges by the FBAs

Figure 11:
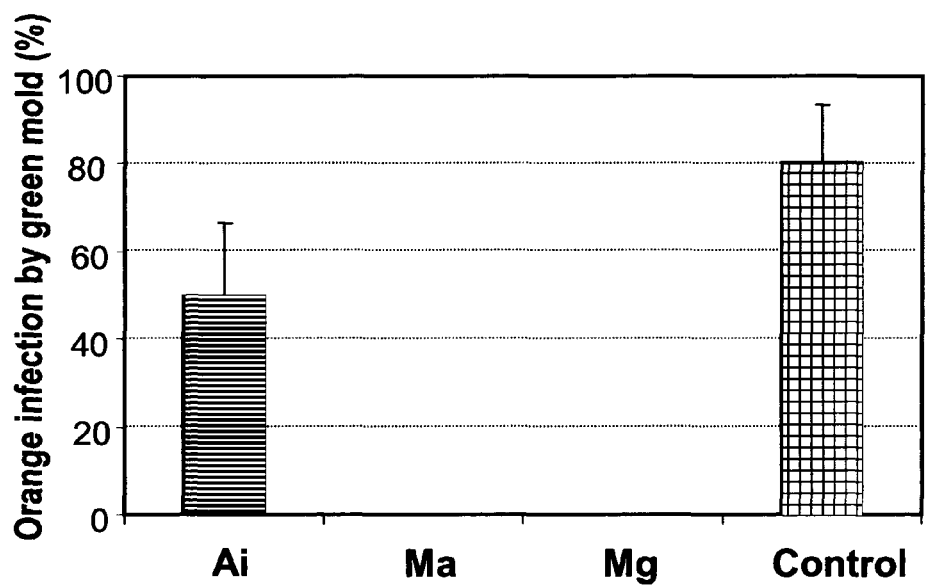
FIG. 11. presents the extent of green mold infection caused by *Pencillium digitatum* to oranges pre-treated by a spray of $1-5\times10^8$ ml$^{-1}$ suspensions of the blastoconidia of *Acaromyces ingoldii* (Ai), *Meira argovae* (Ma) and *Meira geulakonigii* (Mg) in deionized water; control oranges were treated only with deionized water; the extent of infection of the control oranges differed significantly from that of the effect of all FBAs; the vertical lines indicate SE.
Figure 13A:
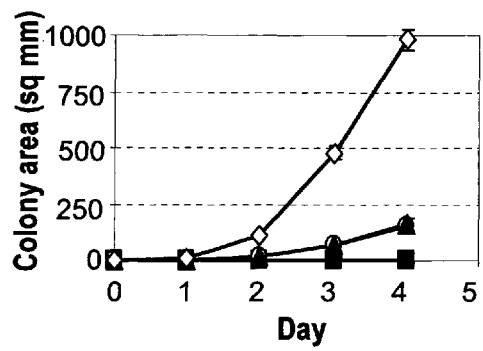
FIG. 13. shows the inhibitory effect of the FBAs on *Pencillium digitatum* (FIGS. 13A and 13C) and on *Sclerotinia sclerotiorum* (FIGS. 13B and 13D), prior to heating in boiling water (FIGS. 13A and 13B) and after heating (FIGS. 13C and 13D); all treatments were significantly different from the controls at $P<0.05$; the vertical lines shows SE.
Figure 13B:
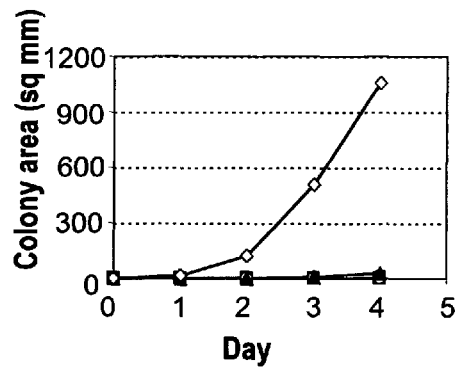
Figure 13C:
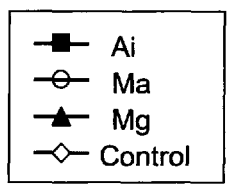
Figure 13C:
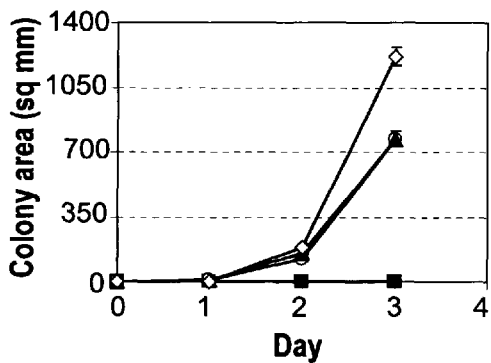
Figure 13D:
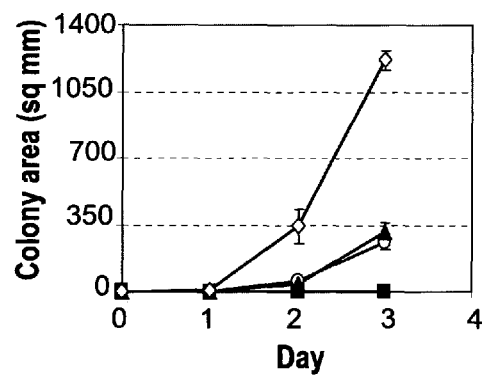

*Meira argovae* and *M. geulakonigii* completely inhibited the development of green mould on the infected oranges, whereas the effect of *A. ingoldii* was far less benign (50% infection), although the damage was still significantly less than in the control fruit (80% infection) (FIG. 11).

The SEM micrographs show that all three FBAs were present on the fruits peel and penetrated it via the stomata (FIG. 12).

Utilization of Carbohydrates (Sugars)

Sugar utilization by the FBAs was quite low, as its depletion by *A. ingoldii* after 10 days came to 15.6% (as compared to the controls), by *Meira argovae* to 14.5% and by *M. geulakonigii* to 21.9%. This suggests that competition for hydrocarbons is, at most, a minor factor affecting pathogen inhibition by the FBAs.

Effect of Proteases Secreted by the FBAs

Weak haloes of ca 1-2 mm developed after one-two weeks of incubation in the dishes containing the FBA mycelia, whereas no haloes appeared in dishes with PDB (data not shown). This indicates the production of external protease by the mycelia of both FBAs assayed. On the other hand, no haloes (meaning no protease secretion) were seen in the assays with the blastoconidia presence suggesting that the latter do not produce proteases.

Effect of Micro-Molecules Produced by the FBA.

The denaturation of the micro-molecules—caused by the boiling water bath—significantly decreased the inhibitory effect of *M. argovae* and of *M. geulakonigii* on *S. sclerotiorum* and *P. digitatum*, as compared with the controls (FIG. 6). However, considerable, significant inhibition remained. On the other hand, the boiling treatment did not reduce the inhibitory activity of the *A. ingoldii* extract plates, indicating that different secondary compounds were secreted by this fungus.

Boiling the protein micro-molecules produced by *M. argovae* and *M. geulakonigii* had no inhibitory effect on the rate of growth of *A. tumefaciens*, as similar haloes of inhibition developed in the microbial colonies exposed to the boiled and to the non-boiled extracts (data not shown).

Fungi used in the biological control of plant pathogens use a variety of antagonistic methods, including parasitism, competition for living space and for nutrient sources, changing the chemical environment, the secreting of toxic or inhibiting secondary compounds and compounds that induce the production of host-plant resistance factors (Agrios 2005; Elad 2000). The fact that all pathogens which were placed on pristine PDAC, after exposure to the FBA extracts, resumed normal growth, strongly suggests that the adverse effect of the FBAs is probably fungistatic. This hypothesis is supported by the observation that conidia of *P. digitatum* that had hitherto failed to develop on the extract dishes, germinated and formed normal mycelia when placed on extract-free PDAC, and by the short-term effect of the FBAs on *S. sclerotiorum* infecting tomato leaves. In addition, the inhibitory effect of the FBA extracts appears to be dosage-dependent, as seen by the decline of inhibition when more sclerotia were placed in a dish.

Many antagonistic fungi inhibit the development of pathogens by competition for nutrients; for instance, *Ulocladium atrum* (Preuss) Sacc. is known to utilize available dietary resources faster than *S. sclerotiorum*, and thereby to control the latter. Our preliminary data on the possible modes of action of the FBAs indicate that competition for sugars most likely does not play a role in the inhibition of pathogen growth. It is known that some antagonistic fungi secrete proteases in order to harm pathogens; for instance, *Trichoderam harzianum* Rifai secretes proteases that reduce the activity of the pathogen *B. cinerea*. As to the FBAs, a rather minor role may at best be allocated to the excretion of proteases. As to macro-molecules, boiling suggests that they are likewise not involved, but micro-molecules cannot be ruled out, because they decreased the inhibitory effect of the two *Meira* spp. (FIG. 13).

Figure 8:
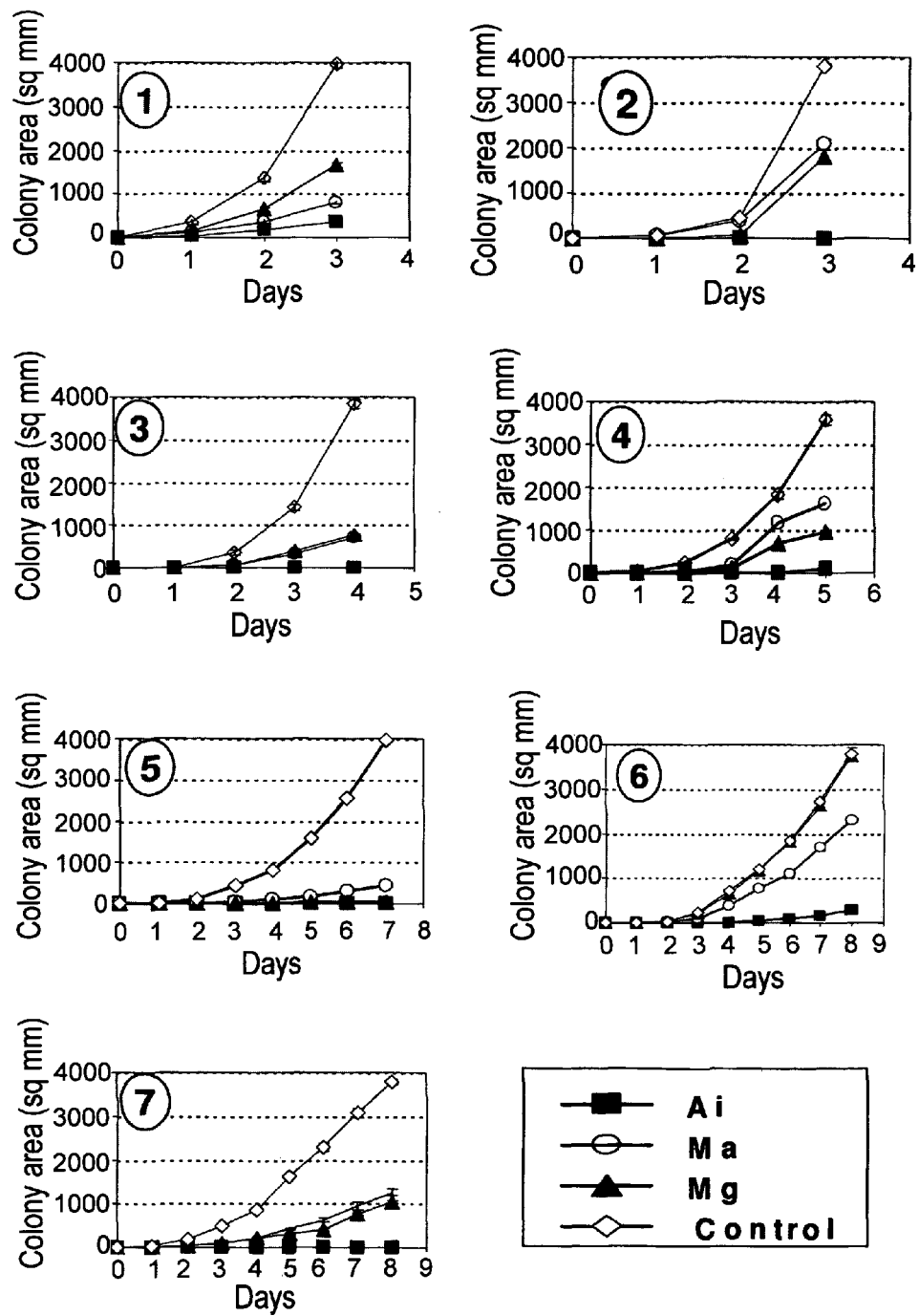
FIG. 8. shows the effect of extracts, prepared from the dishes on which *Acaromyces ingoldii* (Ai), *Meira argovae* (Ma) and *Meira geulakonigii* (Mg) had developed, on the colony growth of seven phytopathogenic fungi: 1. *Rhizoctonia solani*; 2. *Sclerotium rolfsii*; 3. *Sclerotinia sclerotiorum*; 4. *Colletotrichum gloeosporioides*; 5. *Pencillium digitatum*; 6. *Fusarium mangiferae* and 7. *Phytophthora citrophthora*. All treatments were significantly different from the controls at $P<0.05$, except for the effect of *M. geulakonigii* on *F. mangiferae* (6)

We formerly noted (Paz, Gerson, and Sztejnberg 2007a) that each of the three FBAs had a variable effect on several pestiferous mite (Acari) species, and a similar phenomenon was seen in this study. Each of the FBAs affected every pathogen differently, indicating a distinct degree of selectivity which was probably due to their different toxins. The extracts of *A. ingoldii* had the strongest effect on all target-fungi, whereas the influence of the two *Meira* spp. was variable. It is however of interest that whereas the extracts of *A. ingoldii* totally inhibited the colony growth *P. digitatum* (FIG. 8), this FBA afforded oranges significantly less protection against the pathogen than the *Meira* spp. (FIG. 11). Such differences in the effectiveness of FBAs when applying them in the laboratory or in the field are well known.

The penetration of orange stomata (FIG. 12) suggests that, as with grapefruits (Paz, Burdman, Gerson, and Sztejnberg 2007b) the FBAs may live within that fruit's tissues (e.g. are endophytic). The long-term influence of these endophytic FBAs (whose effect, as noted, is mostly fungistatic) is probably due to their continuous secretion of the inhibiting toxins. Backman and Sikora (2008) noted endophytes as an emerging tool for biocontrol, which is consistent with our finding of orange green mould inhibition by the FBAs (especially by *Meira* spp.) (FIG. 11). These micrographs (FIG. 12) suggest that all three FBAs may have an affinity for the conidia and germ tubes of *P. digitatum*, causing their partial collapse.

Subsequent experiments may show whether inoculating citrus fruit with the FBAs could serve as a defense mechanism against fungi.

Formerly we showed that the three FBAs inhibited several species of plant-feeding mites (Gerson, Paz, Kushnir, and Sztejnberg 2005; Paz, Gerson, and Sztejnberg 2007a), and now we broaden this spectrum of susceptible target-pests to phytopathogenic fungi.

Finally, it is of interest that the pathogens, which are assigned to two different Kingdoms: Kingdom Fungi and Kingdom Chromista (Agrios 2005). The former includes taxa of different higher fungal groupings (*C. gloeosporioides, F. mangiferae, P. digitatum* and *S. sclerotiorum* in the Ascomycotina, *R. solani* and *S. rolfsii* in the Basidiomycotina. *Phytophthora citrophthora*, on the other hand, belongs to the Oomycotina in the Kingdom Chromista). Thus it is noteworthy that all were similarly affected by *A. ingoldii* (FIG. 8), whereas the effect of the two *Meira* spp. on the seven pathogens was variable. In addition, the Basimycotine *S. rolfsii* was less hindered by the *Meira* spp. than were the two Ascomycotina pathogens (FIG. 8 and FIG. 9B), suggesting a variable susceptibility to the FBAs. Finally, the wide range of pathogenic fungi that were susceptible to the FBAs suggests that other pathogens (including pathogenic bacteria) may also be inhibited by the FBAs.

While this invention has been described in terms of some specific examples, many modifications and variations are possible. It is therefore understood that within the scope of the appended claims, the invention may be realized otherwise than as specifically described.

REFERENCES

1. Avis, T. and R. R. Bélanger. 2001. Specificity and mode of action of the antifungal fatty acid cis-9-heptadecenoic acid produced by *Pseudozyma flocculosa*. Appl. Environ. Microb. 67:956-960.
2. Backman, P. A. and Sikora, R. A. 2008. Endophytes: An Emerging Tool for Biological Control. Biological Control 46:1-3.
3. Boekhout T., B. Theelen, J. Houbraken, V. Robert, G. Scorzetti, A. Gafni, U. Gerson and A. Sztejnberg. 2003. Novel anamorphic mite-associated fungi belonging to the Ustilaginomycetes: *Meira geulakonigii* gen. nov., sp. nov., *Meira argovae* sp. nov. and *Acaromyces ingoldii* gen. nov., sp. nov. Int. J. Syst. Evol. Micr. 53:1655-1664.
4. Cheng, Y., D. J. McNally, C., Labbe, N. Voyer, F. Belzile and R. R. Belanger. 2003. Insertional mutagenesis of a fungal biocontrol agent led to discovery of a rare cellobiose lipid with antifungal activity. Appl. Environ. Microb. 69:2595-2602.
5. Choi, T. and E. Ma. 2007. Simple and Regioselective Bromination of 5,6-Disubstitutedindan-1-ones with $Br_2$ Under Acidic and Basic Conditions. Molecules 12:74-85.
6. da Silva, C. H. T. P. Leiria, V. C. Carvalho, I. and Taft, C. A. 2006. Molecular modeling, docking and ADMET studies applied to the design of a novel hybrid for treatment of Alzheimer's disease. Journal of Molecular Graphics and Modelling. 25: 169-175.
7. Duffy, B. K. and G. Defago. 1999. Environmental factors modulating antibiotic and siderophore biosynthesis by *Pseudomonas fluorescens* biocontrol strains. Appl. Environ. Microb. 65:2429-2438.
8. Gerson, U. A. Gafni, Z. Paz and A. Sztejnberg. 2008. A tale of three acaropathogenic fungi in Israel: *Hirsutella, Meira* and *Acaroinyces*. Exp. Appl. Acarol. 46:183-194.
9. Gerson, U., Paz, Z., Kushnir, L. and Sztejnberg, A. 2005. New Fungi to Control Phytophagous Mites and Phytophatogenic Fungi. IOBC/WPRS Bulletin 28(1), pp. 103-106.
10. Kanemitsu, K., Nishini, T., Kunishima, H., Okamura, N, Takemura, H., Yamamoto, H. and Kaku, M. (2001) Quantitative Determination of Gelatinase Activity Among Enterococci. Journal of Microbiological Methods 47, pp. 11-16.
11. Paz, Z., Gerson, U. and Sztejnberg, A. (2007a) Assaying Three New Fungi Against Citrus Mites in the Laboratory, and a Field Trial. BioControl 52: 855-862.
12. Paz, Z., S. Burdman, U. Gerson and A. Sztejnberg. 2007b. Antagonistic effects of the endophytic fungus *Meira geulakonigii* on the citrus rust mite *Phyllocoptruta oleivora*. J. Appl. Microbiol. 103:2570-2579.
13. Poola, N. R., Bhuiyan, D., Ortiz, S. Savant, I. A., Sidhom, M., Taft, D. R Kirschenbaum, H. and Kalis, M. 2002. A Novel HPLC Assay for Pentamidine: Comparative Effects of Creatine and Inulin on GFR Estimation and Pentamidine Renal Excretion in the Isolated Perfused Rat Kidney. Journal of Pharmacy and Pharmaceutical Sciences 5: 135-145.
14. Singh, R., A. Kumar and N. Anans. 1989. Phenylethylamines in a rigid framework: synthesis & stereochemical assignments of cis- & trans 5,6-dihydroxy-2-amino-2,3,-dihydro-1H-inden-1-ols. Indian. J. Chem. B. Org. 28:5-9.
15. Somers-Edgar, T. J. and R. J. Rosengren. 2009. Coenzyme $Q_0$ induces apoptosis and modulates the cell cycle in estrogen receptor negative breast cancer cells. Anti-Cancer. Drug. 20:33-40.
16. St Leger, R. J., Nelson J. O. and Screen S. E. 1999. The entomopathogenic fungus *Metarhizium anisopliae* alters ambient pH, allowing extracellular protease production and activity. Microbiology 145:2691-2699.
17. Sztejnberg, A., Paz, Z., Boekhout, T., Gafni, A. and Gerson, U. (2004) A new Fungus with Dual Biocontrol Capabilities: Reducing the Numbers of Phytophagous Mites and Powdery Mildew Disease Damage. Crop Protection 23: 1125-1129.
18. Vey, A., R. E. Hoagland, and T. M. Butt. 2001. Toxic metabolites of fungal biocontrol agents, p. 311-346 In J. Butt and N. Magan (ed.), Fungi as biocontrol agents: progress, problems and potential. CABI publishing Oxfordshire, U.K.
19. Yang, R., H. Yongchao, L. Guoqing, J. Daohong and H. Hung-Chang.
2008. Effects of ambient pH and nutritional factors on antifungal activity of the mycoparasite *Coniothyrium minitans*. BioControl. 44:116-127.

The invention claimed is:
1. A method of controlling mite-associated infestation in a plant susceptible thereto, comprising applying onto the plant or in the vicinity of said plant infested with mites a composition comprising a compound of formula I

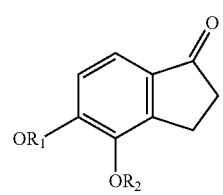

wherein R1 and R2 are independently selected from H, $C_{1-18}$ alkyl, and $C_{1-18}$ acyl.

2. A method according to claim 1 comprising a pesticidal composition, comprising a compound of formula I

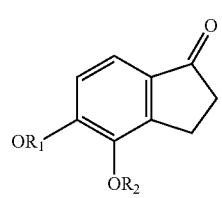

I wherein R1 and R2 are independently selected from H, $C_{1-18}$ alkyl, and $C_{1-18}$ acyl, and at least one component selected from the group consisting of agriculturally acceptable carrier, diluent, emulsifier, dispersant, and an additional active ingredient selected from herbicides, insecticides, growth stimulators, and fertilizers.

3. A method according to claim 1, wherein said plant comprises fruit, vegetable, or ornamental flower.

4. A method of controlling mite infestation according to claim 1, further comprising applying onto the plant or in the vicinity of said plant a composition comprising an extract of a fungus selected from *Meira argovae, Meira geulakonigae,* and *Acaromyces ingoldii*.

* * * * *